United States Patent [19]
Arkles et al.

[11] Patent Number: 4,577,039
[45] Date of Patent: Mar. 18, 1986

[54] METHOD OF PREPARING HEXAMETHYLCYCLOTRISILAZANE

[75] Inventors: Barry C. Arkles, Ambler; Burrell N. Hamon, Fairless Hills, both of Pa.

[73] Assignee: Petrarch Systems Inc., Bristol, Pa.

[21] Appl. No.: 755,049

[22] Filed: Jul. 15, 1985

[51] Int. Cl.[4] ............................................. C07F 7/10
[52] U.S. Cl. .................................................... 556/409
[58] Field of Search ......................................... 556/409

[56] References Cited
U.S. PATENT DOCUMENTS 2,885,370  5/1959  Groszos et al. ................. 556/409 X
3,228,895  1/1966  Burks et al. ..................... 556/409 X
3,230,242  1/1966  Fink .................................... 556/409

Primary Examiner—Paul F. Shaver
Attorney, Agent, or Firm—Panitch Schwarze Jacobs & Nadel

[57] ABSTRACT

Cyclotrisilazanes, including hexamethylcyclotrisilazane, a difunctional blocking agent used to derivatize and protect active hydrogen-containing substrates during chemical analysis and synthetic reactions, may be prepared by heating cyclotetrasilazanes using a Group VIII catalyst in the presence of hydrogen. In addition, the average degree of polymerization of cyclosilazane compositions may be reduced.

14 Claims, No Drawings

METHOD OF PREPARING HEXAMETHYLCYCLOTRISILAZANE

BACKGROUND OF THE INVENTION

The present invention relates to the preparation of hexamethylcyclotrisilazane from octamethylcyclotetrasilazane. Hexamethylcyclotrisilazane is useful as a difunctional blocking agent which is employed to derivatize and to protect various substrates during chemical analysis and synthetic reactions.

Silane blocking agents are used to replace active hydrogens with silyl groups. The silyl derivatives of various alcohols, carboxylic acids, phenols, amino acids, carbohydrates and amines may be more volatile than the corresponding active hydrogen containing substrates and consequently more easily analyzable by gas chromatography. In addition, silane blocking agents are very useful synthetic intermediates, because replacement of active hydrogens with silyl groups often affords products which are more chemically stable and which undergo subsequent chemical reaction at sites other than the silyl blocked site. Hydrolysis of the silyl blocked site will subsequently regenerate the unprotected active hydrogen functionality.

The most commonly used monofunctional silane blocking agent used for silylation is hexamethyldisilazane. This compound reacts with protic species such as alcohols, phenols, carboxylic acids, amino acids, carbohydrates, thiols and amines yielding the silylated derivatives and ammonia as a by-product. Difunctional silane blocking agents are available to selectively block primary amines, vic-diols and other difunctional sites, typically yielding 5-, 6-, and 7-membered silicon-containing rings which are very stable to hydrolysis, oxidation and reduction. This process is termed cyclosilylation.

Examples of effective difunctional silane blocking agents for rigid molecules such as steroids, salicylic, thiosalicylic and anthranilic acids are dimethyldiacetoxysilane and dimethyldimethoxysilane. A more broadly useful technique for cyclosilylation is reaction with hexamethylcyclotrisilazane which forms stable blocked derivatives without formation of polymeric by-products and without need for bulky groups to be present on the substrate compound as discussed in L. Birkofer and O. Stuhl, *J. Organomet. Chem.*, 177, C16 (1979); Ibid. 164, C16 (1979).

Hexamethylcyclotrisilazane may be prepared by the direct ammonolysis of dimethyldichlorosilane. S. D. Brewer, C. P. Haver, *J. Am. Chem. Soc.*, 70, 3888 (1948). However, direct ammonolysis yields a mixture of hexamethylcyclotrisilazane and octamethylcyclotetrasilazane. Hexamethylcyclotrisilazane may be separated from the reaction mixture by fractionation. It is desirable to maximize the proportion of cyclic trimer obtained per unit of raw materials.

Other cyclic silazanes may be prepared by direct ammonolysis of substituted dihalosilanes. For example, U.S. Pat. No. 2,885,370 discloses that cyclic trisilazanes may be prepared by reaction of dicarbocylic dihalosilane such as diphenyldichlorosilane, dihexyldichlorosilane, di-p-tolyldichlorosilane, diphenyldibromosilane, and the like, with ammonia, either in anhydrous ammonia, or in an inert anhydrous liquid medium. Hexaethylcyclotrisilazane and octaethylcyclotetrasilazane are also reported by Brewer et al. U.S. Pat. No. 3,481,964 discloses the preparation of cyclotetrasilazane and cyclotrisilazanes by an analogous process, wherein the dihalogen silane may be substituted with aryloxy, alkenyl including vinyl, aryloxy et al. Octamethylcyclotetrasilazane may be prepared by heating hexamethylcyclotrisilane and hexamethyldisilazane with ammonium chloride. Brewer et al. The oligomerization and polymerization of hexamethylcyclotrisilazane is reviewed in E. G. Rochow, *IUPAC Organosilicon Chemistry* (1966) pp. 247–262.

Recently the catalytic activation of the Si-N bond as a means of producing high molecular weight oligomers containing the —(CH$_3$)$_2$SiNH— unit has been described. M. T. Zoeckler, R. M. Laine, *J. Org. Chem.*, 48, 2539 (1983); R. M. Laine, Y. Blum, A.C.S. Spring Meeting Preprints (May 1, 1985). Using ruthenium carbonyl, Ru$_3$(CO)$_{12}$, as a catalyst to promote activation of Si-N bonds, linear oligomers have been prepared from mixtures of octamethyltetrasilazane and hexamethyldisilazane. Polymers prepared by this method may be pyrolytically converted to yield silicon nitride and silicon carbide nitride. D. Seyferth and G. H. Wiseman, *Prepr. of the Polymer Chemistry Div.* A.C.S. 10 (1984).

SUMMARY OF THE INVENTION

The present invention relates to a process for the preparation of cyclotrisilazanes from cyclotetrasilazanes. This process may use commonly available and relatively inexpensive catalysts such as activated nickel and carbon-adsorbed platinum to convert cyclotetrasilazanes, such as octamethylcyclotetrasilazane, a by-product formed in the preparation of hexamethylcyclotrisilazane, to cyclotrisilazanes, such as hexamethylcyclotrisilazane itself. Alternatively, another Group VIII metal catalyst such as ruthenium carbonyl may be employed in the process.

The process comprises heating cyclotetrasilazane in the presence of hydrogen and a catalyst selected from the Group VIII metal catalysts, including nickel, platinum, and ruthenium. Subsequently, a distillate containing trisilazane may be obtained. In addition, this process may be used to reduce the average degree of polymerization of polymeric cyclosilazane compositions comprising cyclosilazane species having a degree of polymerization of at least 4.

DETAILED DESCRIPTION OF THE INVENTION

Hexamethylcyclotrisilazane is a broadly useful reagent for cyclosilylation of substrates which contain suitable difunctional active hydrogen sites such as primary amines and vic-diols. Specific examples of substrates which may be cyclosilylated include diols of formulas RCH$_2$CH(OH)CH$_2$(OH);

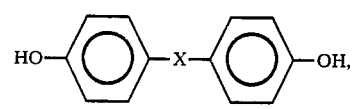

where X is S, SO$_2$; and

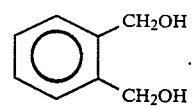

L. Birkofer and O. Stuhl, "Silylated Synthons", *Topics in Current Chemistry* 88, (Springer-Verlag, Berlin 1980) 78.

This reagent yields stable blocked derivatives without the formation of polymeric by-products and without the need for bulky moieties to be present on the substrates as are required in the case of difunctional blocking agents such as dimethyldimethoxysilane. The preparation of hexamethylcyclotrisilazane by direct ammonolysis of dimethyldichlorosilane yields a mixture of the desired cyclic trimer and a by-product, octamethylcyclotetrasilazane, the cyclic tetramer. The cyclic trimer has a boiling point of 188° C. (at 756 mm of Hg) whereas the cyclic tetramer has a boiling point of 225° C. (at 756 mm of Hg). Consequently, these may be separated by fractional distillation.

The present invention affords a method of converting the cyclic tetramer by-product of the direct ammonolysis reaction to the desired cyclic trimer. This is accomplished by heating the cyclic tetramer in the presence of hydrogen and in the presence of a catalyst selected from the Group VIII catalysts.

The cyclic tetramer may be any organo-substituted cyclotetrasilane, such as those disclosed, for example, in U.S. Pat. No. 3,481,964. The cyclic tetramer may be represented by the formula $$(R^1R^2SiNH)_4$$

where $R^1$ and $R^2$ are independently hydrogen or organic radicals. Thus $R^1$ or $R^2$ may be independently chosen from H, alkyl, alkenyl, alkynyl, alkoxy, cycloalkyl, cycloalkenyl, aryl, arylalkyl, aryloxy, dialkylamino, and tri- and di-alkyl silyl. For example, $R^1$ and $R^2$ may be chosen independently from $(C_1-C_6)$alkyl, $(C_1-C_6)$alkenyl, $(C_1-C_6)$alkoxy, $(C_5-C_{10})$cycloalkyl, $(C_6-C_{10})$cycloalkenyl, $(C_6-C_{12})$aryl, $(C_6-C_{12})$aryl-$(C_1-C_4)$alkyl, di$(C_1-C_6)$alkylamino, di- and tri-$(C_1-C_6)$alkyl silyl, and $(C_6-C_{12})$aryloxy. Examples of $R^1$ and $R^2$ include methyl, ethyl, n-propyl, n-butyl, tert-butyl, octyl, vinyl, allyl, methoxy, ethoxy, tert-butoxy, cyclohexyl, phenyl, p-tolyl, benzyl, phenoxy, dimethylamino, diethylamino, dipropylamino, dimethylsilyl, diethylsilyl and trimethylsilyl. Further, the individual silicon atoms in the mer units of the tetramer may bear $R^1$ and $R^2$ substituents which may be the same as those of other mer units in the molecule or they may be different. Within the scope of this invention, it is obvious that $R^1$ and $R^2$ may be any group which is compatible with the cyclosilazane structure and with the reaction conditions of the present invention.

In one embodiment, the reaction mixture is heated while slowly passing hydrogen gas through the mixture to a temperature at which hexamethylcyclotrisilazane distills from the reaction mixture (about 187°–201° C.). In another embodiment the reaction mixture is heated at a temperature of from about 100° C. to 225° C., preferably about 155° C., under hydrogen in the presence of catalyst, and the resulting hexamethylcyclotrisilazane product is subsequently removed from the reaction mixture by distillation. While the process of the present invention may be carried out in a hydrogen atmosphere, such as under one atmosphere of hydrogen, any essentially moisture-free atmosphere containing hydrogen, as provided for example by a hydrogen sparge, or such as a mixed nitrogen/hydrogen or argon/hydrogen atmosphere, may also be employed.

Hydrogen may be sparged through the reaction flask at a rate of about one milliliter per second, under a positive nitrogen atmosphere. The sparge rate must be sufficient to maintain a hydrogen-activated catalyst.

The catalysts preferred to be used in the process of the present invention are activated nickel, such as that prepared by the Raney process, which is a relatively inexpensive catalyst, and platinum adsorbed on a support such as carbon granules, and other supported catalysts which may be recovered by separation from the reaction mixture as by decantation, filtration or the like, and reused in the same process to convert additional cyclotetrasilazane to cyclotrisilazane. Catalysts which may be employed in the process of the present invention include the Group VIII transition metal catalysts, including the Group VIII transition metal carbonyls, such as ruthenium carbonyl, $Ru_3(CO)_{12}$. However, use of inexpensive catalysts such as activated nickel, or a catalyst which may be recycled, such as platinum adsorbed on carbon, is preferred.

Examples of supports which may be employed in preparing the catalyst used in the process of the present invention include diatomaceous silica, activated carbons, such as those derived from soft coal, charcoal, or other carbonaceous material such as prepared by partial oxidation or otherwise, silicates, such as sepiolite, clays such as kaolin and bentonite, silica, alumina, magnesia and their mixtures, molecular zeolites (crystalline aluminosilicates), silicon carbide, zirconia, calcium carbonate, and barium sulfate. Supported metal catalysts may be prepared using any of the techniques commonly known in the art such as adsorption from solution, impregnation, such as by filling the pores of a preformed support with a solution of a metal salt, evaporating the solvent and then decomposing or reducing the metal salt, deposition, precipitation, or coprecipitation. Examples of supported Group VIII transition metal catalysts include platinum-alumina, platinum-polyamide, platinum-carbon molecular seive, platinum-zeolite, platinum-silica, palladium-polyacrylonitrile, palladium-alumina, palladium-silica, palladium-carbon, nickel-silica, rhodium-silica, and irridium-silica. The preparation and characterization of supported metal catalysts is reviewed by R. L. Moss in *Experimental Methods in Catalytic Research* Vol. 2 (Academic Press, New York, 1976) 43–94. In selecting a supported Group VIII transition metal catalyst for the process of the present invention it is desirable to select the particle size of the support so that the supported catalyst may be readily and easily recovered from reaction flask residues subsequent to its use in the process of the present invention. However, as is well known in the art, the particle size of the support must be chosen as a compromise between extreme fineness with a possible improved catalyst performance and a coarser powder that can be more easily separated from the reaction product by filtration.

By "Group VIII metal" is meant a transition metal classified in Group VIII of the periodic table of the elements, including iron, cobalt, nickel, ruthenium, rhodium, palladium, osmium, iridium and platinum. By "Group VIII metal catalyst" is meant the metals themselves, and compounds and complexes derived from the Group VIII metals, such as the metal carbonyls, which are known to the art to be catalytically active in organic chemical reactions.

The catalyst may be used in catalytically effective amounts in the reaction mixture. About one percent by weight of the reaction mixture of a catalyst such as 5% platinum on carbon, giving about 0.05% by weight platinum based on the total weight of the reactants, may be used. However, lesser amounts of catalyst may be used, such as about 0.1% by weight of the reaction mixture of a catalyst such as 5% platinum on carbon. Because the catalyst is the most costly component of the reaction mixture, the preferred amount is the minimum which effectively catalyzes the reaction, as easily determined by those skilled in the art with a minimum of experimentation.

Octamethylcyclotetrasilazane, hexamethylcyclotrisilazane and other silazanes are moisture sensitive compounds and it is desirable to maintain them in moisture-free environments such as a dry nitrogen atmosphere.

In addition to its use in converting octamethylcyclotetrasilazane to hexamethylcyclotrisilazane, the process of the present invention may be used to convert compositions containing higher cyclic and/or linear oligomers and/or polymers of the —$R^1R^2SiNH$— unit to compositions containing lower average degrees of polymerization where $R^1$ and $R^2$ are defined as above. For example, equimolar mixtures of cyclic trimer and cyclic tetramer, which are characterized by a degree of polymerization of 3.5, may be converted to mixtures having a degree of polymerization of less than 3.5. Similarly, the relative proportion of higher mer species such as cyclic pentamer, cyclic hexamer and the like may be reduced in compositions containing a distribution of mer species by the process of this invention. In general the polymeric composition should be heated to a temperature above its melting point in order to provide an intimate mixture of silazane, hydrogen and catalyst.

The invention will now be illustrated in more detail by reference the following specific, nonlimiting examples.

EXAMPLE 1

A 500 ml flask is fitted with a gas inlet tube for the introduction of hydrogen, a thermometer, a short, heated distillation column, and a distillation head vented through a dry nitrogen bypass. The flask is charged with 250 g of octamethylcyclotetrasilazane and 1.25 g of a catalyst consisting of 5 wt% platinum on carbon granules having an effective surface area of 1000 $m^2/g$. The mixture is then heated using a heating mantle while slowly passing hydrogen gas through the mixture to a temperature at which hexamethylcyclotrisilazane distills from the reaction mixture as formed. 151 g of distillate containing 128 g of hexamethylcyclotrisilazane is collected over a 24 hour period. Subsequently, an additional 300 g of octamethylcyclotetrasilazane and 3 g of the same catalyst is charged to the reaction flask containing the residue of the initial reaction and is heated under a stream of hydrogen to give an additional 290 g of distillate containing 248 g of hexamethylcyclotrisilazane. A viscous dark residue of 94 g remains in the reaction flask.

EXAMPLE 2

Using the same reaction apparatus as described in Example 1, 300 g of octamethylcyclotetrasilazane is heated under hydrogen with 3 g of 5 wt% platinum on carbon granule catalyst to yield 230 g of distillate containing 195 g of hexamethylcyclotrisilazane and 23 g of unreacted octamethylcyclotetrasilazane as determined by gas chromatography. 33 g of high boiling oily residue is decanted from the catalyst remaining in the reaction flask. 300 g of octamethylcyclotetrasilazane is charged to the flask with the catalyst residue and is heated under hydrogen to yield 238 g of distillate containing 206 g of hexamethylcyclotrisilazane. After decanting 52 g of residue, the same catalyst charge is used a third time with an additional 300 g of octamethylcyclotetrasilazane to yield additional hexamethylcyclotrisilazane. In summary total of 900 g of octamethylcyclotetrasilazane is reacted under hydrogen using 3 g of 5 wt% platinum on carbon granule catalyst (Johnson Matthey, steam-activated carbon, surface area of 1000 $m^2/g$) to yield 697 g of distillate (b.p. 187°–201° C. at atmospheric pressure) containing 594 g hexamethylcyclotrisilazane and 71 g of recovered octamethylcyclotetrasilazane and 163 g of high boiling viscous distillation residue (b.p. >300° C. at atmospheric pressure).

EXAMPLE 3

Using the same apparatus as in Examples 1 and 2, 300 g of octamethylcyclotetrasilazane is heated at 155° C. under hydrogen with 17.5 g of dry Raney nickel. After one hour a reaction sample is removed and found to contain 68% hexamethylcyclotrisilazane by gas chromatography. Distillation gives 200 g of distillate (b.p. 187°–201° C. at atmospheric pressure) containing 174 g of hexamethylcyclotrisilazane and 17 g of recovered octamethylcyclotetrasilazane.

EXAMPLE 4

A 500 ml, three neck flask, equipped with a fritted gas sparge tube, condensor, magnetic stirrer, and heating mantle is charged with 120 g of octamethylcyclotetrasilazane. The octamethylcyclotetrasilazane is heated above its melting point and a slow hydrogen sparge is initiated. After the flask is purged of air, 0.2 g of ruthenium carbonyl $Ru_3(CO)_{12}$ is added. In approximately 15 minutes a sample of the reaction mixture is drawn and analyzed. Analysis by gas chromatography indicates the mixture contains 70–72% hexamethylcyclotrisilazane and 20–21% of octamethylcyclotetrasilazane. The remaining material appears to be a series of higher boiling homologues of these compounds.

The present invention may be embodied in other specific forms without departing from the spirit or essential attributes thereof and, accordingly, reference should be made to the appended claims, rather than to the foregoing specification as indicating the scope of the invention.

We claim:

1. A process for the preparation of cyclotrisilazane comprising heating cyclotetrasilazane in the presence of hydrogen and a catalyst selected from the Group VIII metal catalysts.

2. The process of claim 1 wherein said cyclotetrasilazane is selected from tetrasilzanes of the formula $(R^1R^2SiNH)_4$ wherein $R^1$ and $R^2$ are independently selected from H, alkyl, alkenyl, alkoxy, cycloalkyl, cycloalkenyl, aryl, arylalkyl, aryloxy, dialkyl amino and di- and tri-alkyl silyl.

3. The process of claim 2 wherein said cyclotetrasilazane is octamethylcyclotetrasilazane and said process yields hexamethylcyclotetrasilazane.

4. The process of claim 3 wherein said octamethylcyclotetrasilazane is heated at a temperature of from about 97° C. to 188° C.

5. The process of claim 1 wherein said catalyst is selected from nickel and platinum.

6. The process of claim 5 wherein said catalyst is platinum adsorbed in carbon granules.

7. The process of claim 5 wherein said catalyst is activated nickel.

8. The process of claim 7 wherein said activated nickel is Raney nickel.

9. The process of claim 1 wherein said Group VIII metal catalyst is a Group VIII metal carbonyl compound.

10. The process of claim 9 wherein said Group VIII metal carbonyl compound is ruthenium carbonyl.

11. The process of claim 3 additionally comprising distilling the reaction mixture resulting from heating said octamethylcyclotetrasilazane and collecting the fraction distilling between about 187° C. and 201° C.

12. The process according to claim 11 additionally comprising separating the catalyst from the distillation residue.

13. The process of claim 12 wherein said separation is performed by decantation of the distillate residue from the catalyst.

14. A process for reducing the average degree of polymerization of an initial polymeric composition comprising species having the formula $(R^1R^2SiNH)_n$, where n is an integer of at least 4, and wherein $R^1$ and $R^2$ are independently selected from H, alkyl, alkenyl, alkoxy, cycloalkyl, cycloalkenyl, aryl, arylalkyl, aryloxy, dialkyl amino and di- and tri-alkyl silyl, comprising heating said initial polymeric composition in the presence of hydrogen and a catalyst selected from the Group VIII metal catalysts at a temperature greater than the melting point of said initial polymeric composition.

* * * * *